United States Patent
Beck et al.

(10) Patent No.: US 9,254,100 B2
(45) Date of Patent: Feb. 9, 2016

(54) LOGGING DAILY AVERAGE METABOLIC ACTIVITY USING A MOTION SENSOR

(75) Inventors: Kenneth Beck, St. Paul, MN (US); Ramesh Wariar, Blaine, MN (US); Chie Kawahara, Minneapolis, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2288 days.

(21) Appl. No.: 11/900,596

(22) Filed: Sep. 12, 2007

(65) Prior Publication Data

US 2009/0069720 A1 Mar. 12, 2009

(51) Int. Cl.
*A61B 5/117* (2006.01)
*A61B 5/103* (2006.01)
*A61B 5/11* (2006.01)
*A61B 5/00* (2006.01)

(52) U.S. Cl.
CPC .............. *A61B 5/1118* (2013.01); *A61B 5/4866* (2013.01); *A61B 5/0002* (2013.01)

(58) Field of Classification Search
CPC .................................................. A61B 5/1118
USPC ......... 600/587, 300, 301, 547, 481, 485, 508, 600/595; 340/573.1
See application file for complete search history.

(56) References Cited

U.S. PATENT DOCUMENTS

| | | | |
|---|---|---|---|
| 5,044,366 A * | 9/1991 | Alt .................................. | 607/18 |
| 5,976,083 A * | 11/1999 | Richardson et al. .......... | 600/300 |
| 6,021,351 A | 2/2000 | Kadhiresan et al. | |
| 6,045,513 A | 4/2000 | Stone et al. | |
| 6,135,970 A | 10/2000 | Kadhiresan et al. | |
| 6,168,569 B1 * | 1/2001 | McEwen et al. ............... | 600/557 |
| 6,273,856 B1 | 8/2001 | Sun et al. | |
| 2008/0177191 A1 * | 7/2008 | Patangay et al. .............. | 600/509 |

OTHER PUBLICATIONS

Balogun, J. A., et al., "Energy cost determination using a portable accelerometer", *Phys Ther.*, 66(7), (Jul. 1986),1102-9.
Bouten, C. V., et al., "Assessment of energy expenditure for physical activity using a triaxial accelerometer", *Med Sci Sports Exerc.*, 26(12), (Dec. 1994),1513-23.
Obisesan, T. O., et al., "Energy expenditure and symptom severity in men with heart failure.", *Am J Cardiol.*, 77(14), (Jun. 1, 1996),1250-2.

(Continued)

*Primary Examiner* — Brian Szmal

(74) *Attorney, Agent, or Firm* — Schwegman Lundberg & Woessner, P.A.

(57) ABSTRACT

An implantable activity detector can detect metabolic stress levels, which can be normalized, such as to identify times of activities such as walking and running or to identify trends such as a decrease in metabolic activity. The data can be derived from different sources such as an accelerometer and pedometer. This data can be compared to independently specifiable thresholds, such as to trigger an alert or responsive therapy, or to display one or more trends. The information can also be combined with other congestive heart failure (CHF) indications. The alert can notify the patient or a caregiver, such as via remote monitoring. Metabolic activity data from one or more of the activity detectors can be used to establish a model of metabolic stress, to which further activity data can be compared for identifying periods of increased or decreased metabolic stress.

29 Claims, 7 Drawing Sheets

(56) References Cited

OTHER PUBLICATIONS

Oka, R. K., et al., "Daily physical activity levels in congestive heart failure.", *Am J Cardiol.* Apr. 15, 1993;71(11):,921-5

Ruch, Theodore C., et al., *Physiology and Biophysics*, W.B. Saunders Company, Philadelphia & London,(1965),1036-1037.

Toth, M. J., et al., "Daily energy expenditure in free-living heart failure patients.", *Am J Physiol.*, 272(3 Pt 1), Mar. 1997,E469-75.

Toth, M. J., et al., "Daily energy requirements in heart failure patients.", *Metabolism*, 46(11), (Nov. 1997),1294-8.

Walsh, J T., et al., "Relation of daily activity levels in patients with chronic heart failure to long-term prognosis", *Am J Cardiol*, 79(10), 1997,1364-1369.

* cited by examiner

LOGGING DAILY AVERAGE METABOLIC ACTIVITY USING A MOTION SENSOR

TECHNICAL FIELD

This patent document pertains generally to patient monitoring and more particularly, but not by way of limitation, to monitoring metabolic energy consumption.

BACKGROUND

Patient monitoring can be used for various needs, such as to determine therapy efficacy. Through both long term and short term assessment of patient metabolic energy consumption, physical activity can be correlated with an indication of patient condition or prognosis.

OVERVIEW

An implantable or external activity sensor (e.g., accelerometer) can be used to detect patient activity. A daily average metabolic equivalent (MET) can be calculated from the activity sensor output. Trending daily average METs may provide useful information related to a patient well-being. Without being bound by theory, the present inventors believe that integrating activity sensor output data over a twenty-four hour period can provide better predictive value than certain other approaches, such as measuring a time duration that patient activity exceeds a fixed activity threshold. The information from the activity sensor can be converted into units such as METs, which represents $O_2$ consumption and can be directly related to calories burned. Storing or logging activity sensor output data over a twenty-four hour period permits determining a daily average MET for a subject. Trending the daily average METs can help the patient or caregiver in determining whether patient condition has changed. For example, an increased severity of chronic heart failure (CHF) can correlate to reduced $O_2$ consumption. This can be detected as reduced metabolic activity, such as a decrease in the daily average METs. The daily average METs can be compared to a threshold value and used to generate an alert to notify the patient or a caregiver, such as via remote monitoring. The daily average METs patient status indication can be combined with one or more other patient status indications, such as from one or more additional physiological sensors (e.g., respiration, heart rate, weight, etc.), such as to provide a more complete indication of patient well-being.

Example 1 describes a system comprising an activity detector and a processor circuit, coupled to the activity detector. The activity detector is configured to detect physical activity indication of a subject. The processor is configured to analyze exertion data from the activity detector and the processor is configured to determine a metabolic stress indicator derived from an integration or area under the curve calculation of the measured exertion data occurring during the physical activity within a time period.

In Example 2, the system of Example 1 is optionally configured with the processor providing a normalized average metabolic equivalent indication to a user or automated process.

In Example 3, the system of at least one of Examples 1-2 optionally includes a trending module, operatively coupled to the activity detector and processor circuit. The trending module is configured to trend normalized average metabolic equivalent indication occurring two or more times within a specified duration.

In Example 4, the system of at least one of Examples 1-3 is optionally configured with the activity detector configured to detect a period of sustained physical activity exceeding a specified exertion level and a specified duration.

In Example 5, the system of at least one of Examples 1-4 is optionally configured with the specified exertion level comprising at least 20 mGs.

In Example 6, the system of at least one of Examples 1-5 is optionally configured with the specified duration comprising at least three minutes.

In Example 7, the system of at least one of Examples 1-6 is optionally configured with the activity detector configured to determine a total number of steps per day.

In Example 8, the system of at least one of Examples 1-7 is optionally configured with the activity detector configured to determine a daily average MET using measured exertion data wherein the exertion data is obtained in increments of less than one minute.

In Example 9, the system of at least one of Examples 1-8 optionally includes an alert module, operatively coupled to the activity detector and processor circuit. The alert module is configured to generate an alert indication in response to a change in value of at least one of the exertion data or the normalized average metabolic equivalent indication, wherein the change in value occurs at least once within a specified time duration.

In Example 10, the system of at least one of Example 1-9 optionally configured with the specified time duration comprising at least two days.

Example 11 includes a method comprising detecting physical activity of a subject within a time period, computing exertion data using the detected physical activity within the period, and determining a metabolic stress indicator derived from an indication of an integration or area under the curve of the exertion data over the period.

In Example 12, the method of Example 11 optionally includes providing a normalized average metabolic equivalent indication to a user or process.

In Example 13, the method of at least one of Examples 11-12 is optionally includes trending the normalized average metabolic equivalent indication.

In Example 14, the method of at least one of Examples 11-13 is optionally performed such that detecting physical activity comprises detecting a period of sustained physical activity exceeding a specified exertion level and a specified duration.

In Example 15, the method of at least one of Examples 11-14 is optionally performed such that the specified exertion level comprises at least 20 mGs.

In Example 16, the method of at least one of Examples 11-15 is optionally performed such that the specified duration comprises at least three minutes.

In Example 17, the method of at least one of Examples 11-16 optionally includes determining a step rate derived from an averaged acceleration measurement of the subject movement over the period.

In Example 18, the method of at least one of Examples 11-17 optionally includes deriving a metabolic equivalent (MET) from an acceleration within the period.

In Example 19, the method of at least one of Examples 11-18 is optionally performed such that determining a metabolic stress indicator comprises deriving a step total energy derived from the detected physical activity within the period.

In Example 20, the method of at least one of Examples 11-19 optionally includes measuring at least one physiological parameter during the detected physical activity of the subject, wherein the measured physiological parameter varies with physical activity of the subject, and reporting the physiological parameter measurement to a user or automated process.

In Example 21, the method of at least one of Examples 11-20 is optionally performed such that providing a normalized average metabolic equivalent indication comprises deriving a number representative of average metabolic equivalent (MET) over the period.

In Example 22, the method of at least one of Examples 11-21 optionally includes generating an alert in response to a change in value of at least one of the exertion data or the normalized average metabolic equivalent indication, wherein the change in value occurs at least once within a specified time duration.

In Example 23, the method of at least one of Examples 11-22 is optionally performed such that the specified time duration comprises at least two days.

In Example 24, the method of at least one of Examples 11-23 is optionally performed such that determining a metabolic stress indicator comprises deriving a value representative of a population.

In Example 25, the method of at least one of Examples 11-24 is optionally performed such that determining a metabolic stress indicator comprises deriving a value representative of the subject.

Example 26 describes a system comprising means for detecting physical activity of a subject within a time period, means for computing exertion data using the detected physical activity within the period, and means for determining a metabolic stress indicator derived from an indication of an integration or area under the curve calculation of the measured exertion data over the period.

In Example 27, the system of Example 26 optionally includes means for providing a normalized average metabolic equivalent indication to a user or automated process.

In Example 28, the system of at least one of Examples 26-27 optionally includes means for computing exertion data. The means for computing exertion data comprises applying one or more of a metabolic equivalent (MET) or a step rate obtained from an acceleration measurement of the subject movement.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
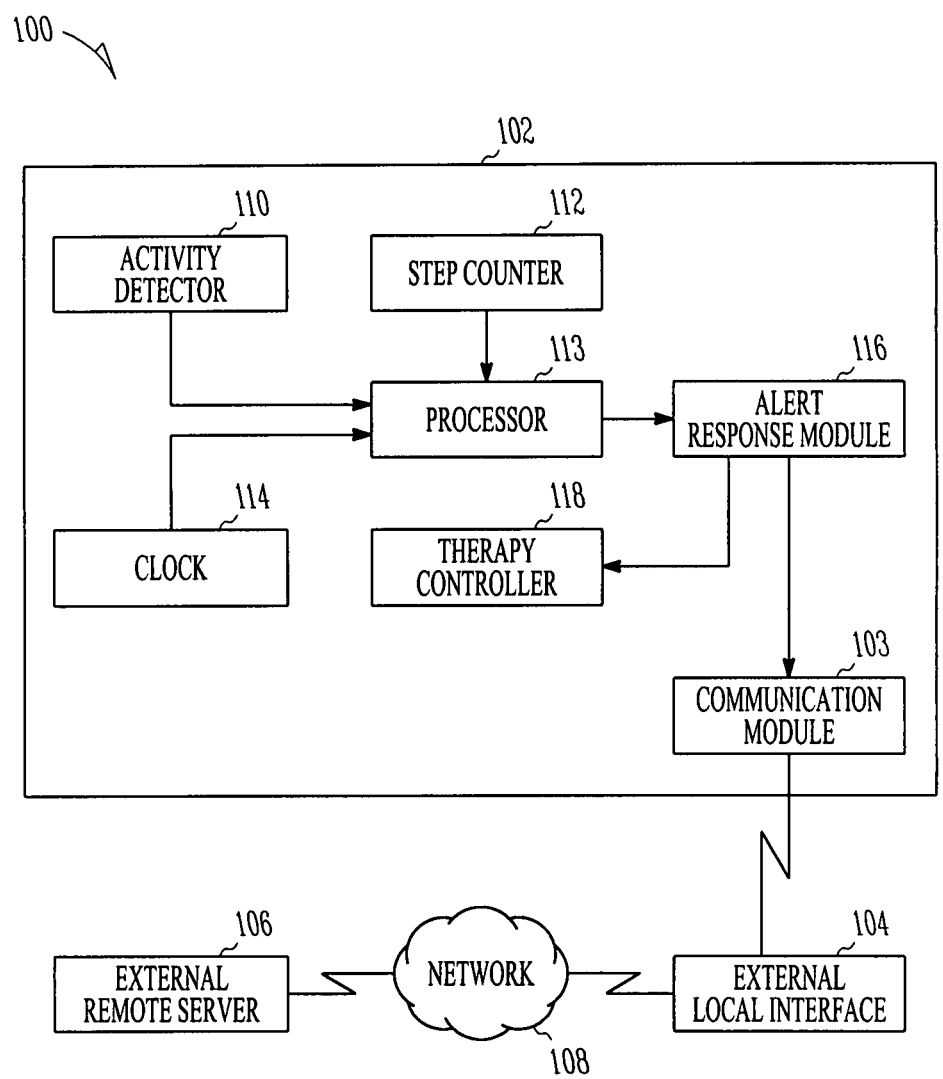
FIG. 1 is a block diagram illustrating generally an example of a system including an implantable device, an external local interface and an external remote server.

FIG. 1 is a block diagram illustrating generally an example of a system 100 including an implantable device 102. The implantable device 102 is typically wirelessly communicatively coupled by a communication module 103 to an external local interface 104. The external local interface 104 can optionally in turn communicatively coupled to an external remote server 106, such as over a wired or wireless telecommunications or a computer network 108. In certain examples, the implantable device 102 includes an implantable cardiac function management device 102, such as a pacer, cardioverter, defibrillator, cardiac resynchronization therapy (CRT) device, or a combination device that combines these or other functions, such as patient monitoring, therapy control, or the like.

In this example, the implantable device 102 can include a hermetically sealed housing to carry electronics, and can include a general activity detector 110, such as a step counter 112, a processor 113, a clock 114, an alert response module 116 and a therapy controller 118. In the example of FIG. 1, the general activity detector 110 transduces a subject's movement into an electrical or other surrogate signal representative of such movement. An example of a general activity detector 110 is an accelerometer, which detects movement of a subject and generates an accelerometer output signal that is indicative of the magnitude and frequency of the movement. In certain examples, the general activity detector 110 can provide information about activity changes or identification of the amount of activity during a given time period, such as when used in conjunction with clock 114 to define the desired time period of interest. In certain examples, a multi-axis accelerometer can be used as the general activity detector 110. The multi-axis accelerometer can provide positional information such as posture of the subject. The multi-access accelerometer can be calibrated for a particular subject. In certain examples, a step counter 112 can be used to identify steps taken by a subject to provide an indication of the subject's physical activity. An example of a step counter 112 can include a pedometer, which detects walking by a subject, and generates a count reflecting an accumulated number of steps taken over a certain period of time. In certain examples, a step counter 112 can be used with a clock 114 to determine a total number of steps taken during a particular time period. This allows identification of time periods of increased or decreased walking. In other examples, certain activities, such as walking, running, stair climbing, etc., can be identified during such periods of increased or decreased step counts or other physical activity levels.

In the example of FIG. 1, the processor 113 can receive input from the general activity detector 110, step counter 112, and clock 114. Based on one or more such inputs, the processor 113 can calculate an indication of daily average physical activity. In certain examples, the alert response module 116 can trend the physical activity indication from the processor over time. The alert response module 116 can communicate the physical activity or trend information, such as to a user interface device of the subject or caregiver, via communication module 103. The trend information from the alert response module 116 supplied to the communication module 103 can be presented in various forms as needed by the user or caregiver. In another example, the alert response module 116 can send an adjustment request to the therapy controller 118 to adjust therapy to the subject, such as based upon application of at least one specified criterion (e.g., comparison of the physical activity trend to a threshold value).

Figure 2:
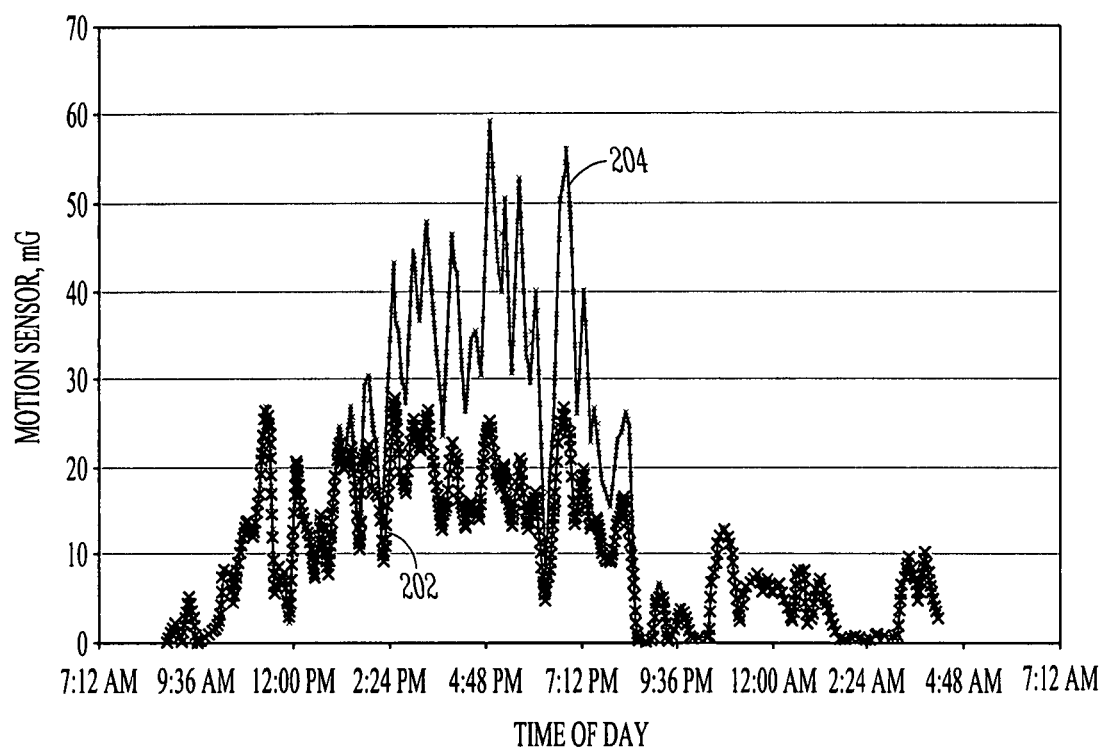
FIG. 2 is a graph illustrating an example of a simulation of motion sensor exertion over time against a baseline.

The information obtained from either the general activity detector 110 or step counter 112 can be used to calculate physiological stress and converted into units more easily understood by those in the medical community, such as METs. In certain examples, the general activity detector 110 can output accelerometer-derived exertion data, which can be expressed in "milliG" or "mG" (where 1 G represents the acceleration of gravity, and 1 mG represents 1/1000 of 1 G). An example of a simulation of such data is represented in the graph of FIG. 2, showing exertion in mGs charted over time. The baseline activity 202 can be compared to the increased activity 204 in order to identify a trend or indication of changed patient condition. Having collected exertion data in mG, the processor 113 can then convert the exertion data into METs using Equation (1):

$$MET = 0.026 * mG + 1.5 \tag{1}$$

Figure 3:
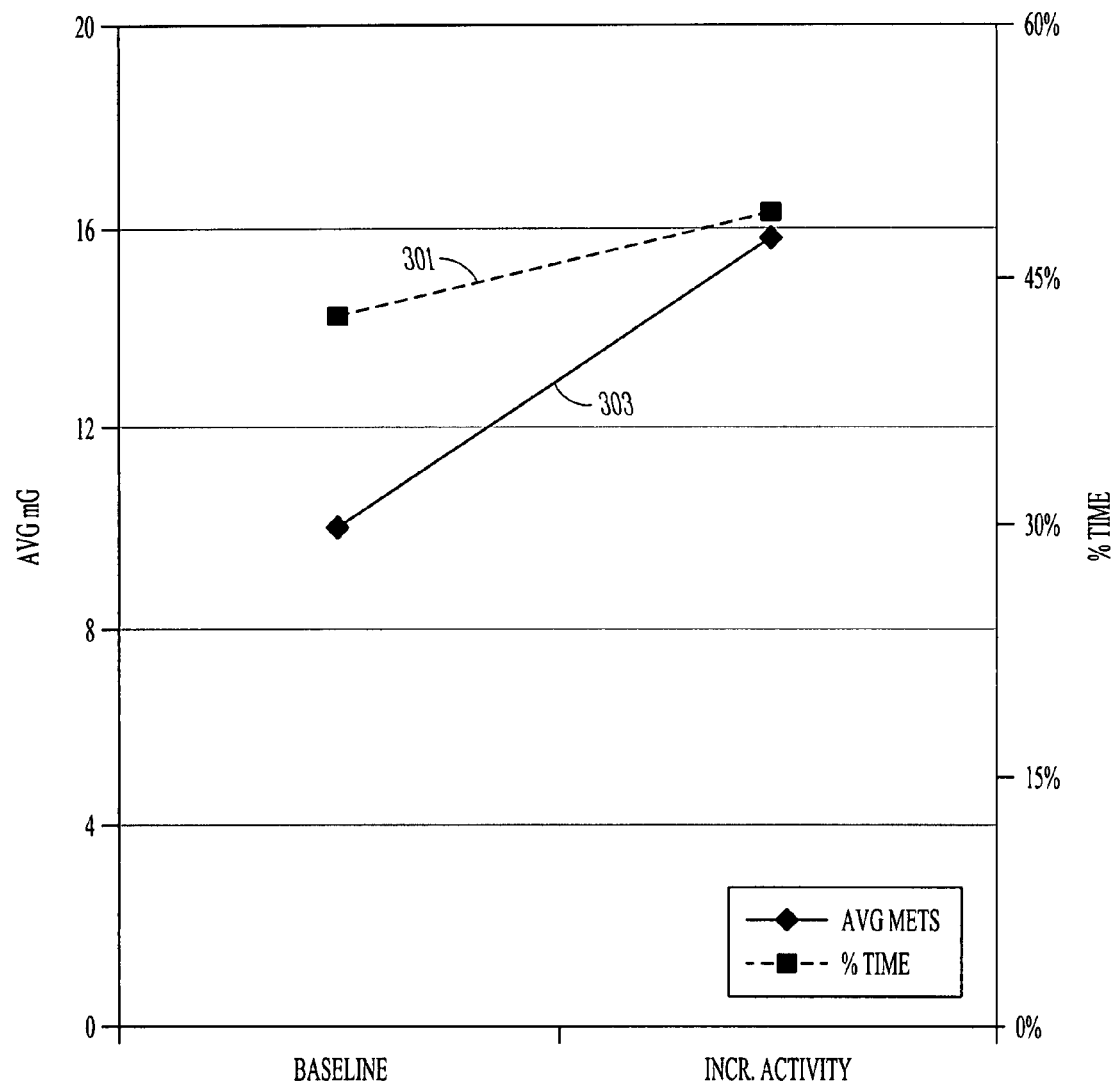
FIG. 3 illustrates a conceptual example of the difference of graphically representing a change in patient activity using percent time over a threshold and daily average METS.

FIG. 3 illustrates a conceptual example of the difference of graphically representing a change in patient activity occurring between a baseline period, represented on the left half of FIG. 3 to that of a period of increased activity, represented on the right half of FIG. 3. Using the simulation data represented in FIG. 2, and setting an activity threshold value to 12 mGs, FIG. 3 illustrates a noticeable difference between two measures: (1) percentage of time spent over the activity threshold value and (2) average METs. In the example of FIG. 3, a first approach monitoring a change in percentage of time spent over an activity threshold value 301 would show an increase of approximately 7-8%. In contrast, a second approach monitoring average METs would show an increase of approximately 5.5 METs, which is a larger relative change than the first approach. An example of exertion data converted into METs is shown in the simulation data graphs of FIGS. 4 and 5.

Figure 4:
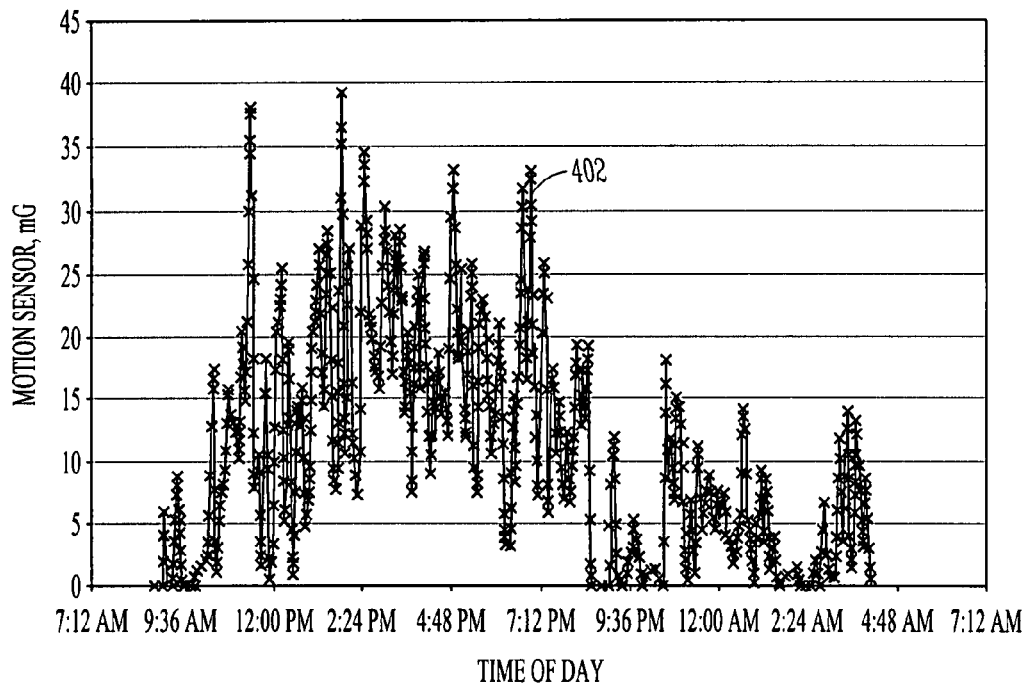
FIG. 4 is a simulation data graph illustrating an example of motion sensor exertion prior to re-scaling.
Figure 5:
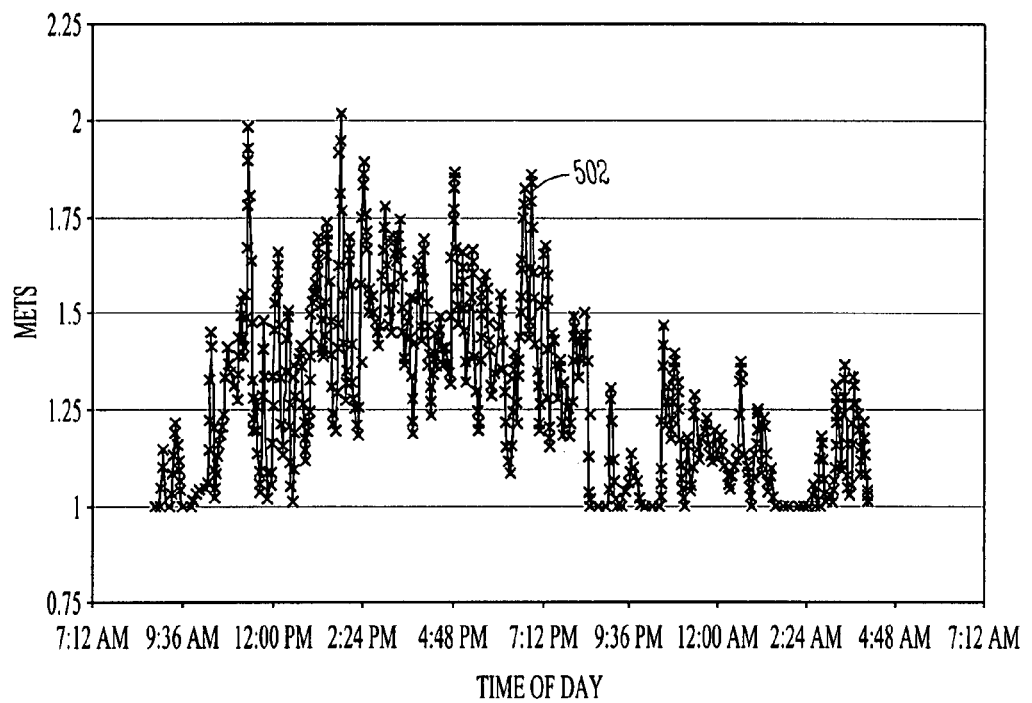
FIG. 5 is a simulation data graph illustrating an example of exertion data in METs converted from measured motion sensor exertion data of FIG. 3.

FIG. 4 illustrates simulated exertion data 402 collected from a general activity detector 110 over a 24 hour period. FIG. 5 illustrates the simulated exertion data 402 of FIG. 4, which has been converted into METs, using Equation (1), illustrated as METs data 502. The conversion does not change the shape of the data, as charted against time, but changes the units into a more clinically understandable metabolic stress value of METs. The alert response module 116 can obtain time data from the processor 113 (via the clock 114) and trend the METs values over a period of time (e.g., daily or 24 hours). In this manner, the alert response module 116 can determine a daily average MET equivalent for exertion of the subject.

In order to determine an overall metabolic stress over a monitored period of time, statistical analysis can be performed on the exertion data from a general activity detector, such as that obtained from an accelerometer or step counter, occurring within a given time period using an area under the curve (AUC) analysis. For example, overall metabolic stress over a monitored period of time can be obtained by multiplying an average METs by the monitored period of time (t), or by integrating a trended indication of METs over the monitored period of time. In certain examples, the step counter 112 can provide data representing total steps over a period or stepping rate (e.g., steps per day). This information can assist the user or caregiver in determining whether the subject's physical activity (e.g., walking) has decreased, which can indicate increased severity of a patient's CHF condition. Using the exertion data from a general activity detector 110 (expressed in mGs), the number of equivalent steps from a step counter 112 can be determined using Equation (2):

$$Steps = 1.274 * AUC - 133 \tag{2}$$

In certain examples, a time-normalized average METs value can be derived by dividing the AUC values by the time period used in the calculations. This value can provide the user or caregiver a daily value with which to monitor metabolic activity of the subject. In certain examples, both total steps and general accelerometer-derived exertion level can be analyzed over the same time period. This allows correlation between the two activity data sources to be ascertained. For example, if an increased generalized accelerometer-derived exertion at 10:30 in the morning occurred at the same time when step activity increased for a period of ½ hour, it can be inferred that the subject took a morning walk for half an hour. In certain examples, METs can be derived from the measured number of steps over a given period of time (t) using Equation (3):

$$METs_{(t)} = 1.274 * \left[\frac{AUC}{t} - 133\right] * 0.026 + 1.5 \tag{3}$$

It may be useful to establish a baseline for a subject, so that the METs value can be compared to a lower bound (e.g., a resting value) and an upper bound (e.g., a maximum value attainable by the subject). In order to establish an upper bound for a subject, one possible expression for physiological metabolic response is "$VO_{2max}$," which refers to a maximum rate of oxygen consumption. $VO_{2max}$ represents the maximum amount of oxygen, in milliliters (ml), that the subject can use in one minute, expressed per kilogram (kg) of body weight. The $VO_{2max}$ for a given subject can be determined using a treadmill or step test in which the subject performs a timed physical test and the weight of the subject is obtained. This number can be converted to METs to represent the maximum metabolic expenditure of the patient. A lower bound can be established by measuring the resting $VO_2$, representing a minimum metabolic expenditure (usually close to 1 MET). The upper and lower bounds can be used to establish a $VO_2$ range, which can be converted into a METs range using Equation (4):

$$MET = \frac{VO_2}{3.5 \, ml * O_2 / min/kg} \tag{4}$$

The METs for a given time (t) can then be compared or viewed with respect to the subject metabolic range to determine where a given daily average fits within that subject's range and further to identify trends in average MET from day to day or month to month.

Additionally, with the incorporation of weight of the subject (in kg), as determined in the $VO_2$ max. determination, the physiological scale of kCals can be determined. KCals represents the energy needed to increase the temperature of 1 kg of water by 1° C., which is one thousand calories. The user or physician may wish to express the physical activity of the subject in kCals using Equation (5):

$$kCal = r * VO_2 * kg \tag{5}$$

The term r represents a conversion factor comprising a range of 4.8 to 5.0. The term kg in Equation (5) represents the subject's weight expressed in kilograms, which may be used from historical data or provided to the implantable device 102 via communication module 103, after weighing the subject.

Figure 6:
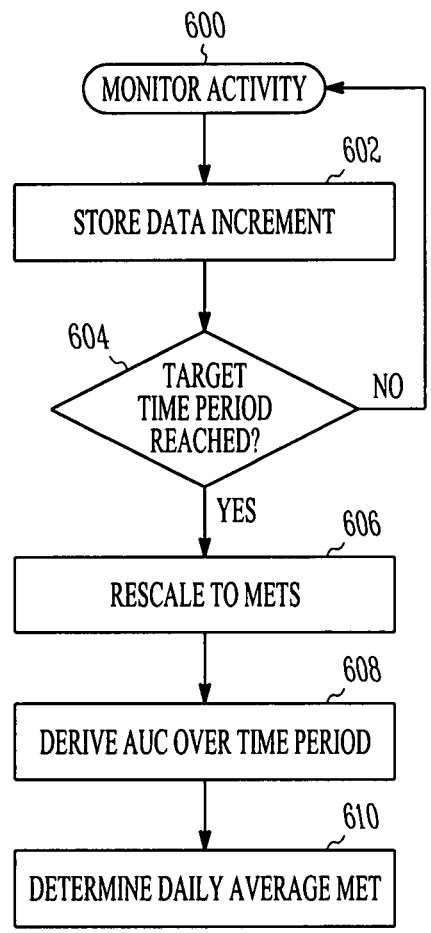
FIG. 6 is a diagram illustrating generally an example of portions of a technique for monitoring average daily metabolic expenditure using an activity monitor.

FIG. 6 is a diagram illustrating generally an example of how a daily average metabolic activity value can be derived from monitoring subject activity. At 600, activity is monitored for exertion levels of the subject, such as walking, running, or riding a bicycle. At 602, data obtained from the generalized accelerometer-derived activity detector (e.g., mGs) is stored and associated with a time of occurrence. In certain examples, data obtained from the detector may be processed in real-time before storage to provide short term detection before a target time is reached. In certain examples, the clock 114 provides input to the processor for generating a time stamp and the information may be either stored in internal memory or communicated via the communication module 103. At 604, if the target time period for determining the daily average METs is reached (e.g., 24 hours have passed), then at 606, the stored exertion data is converted to METs equivalent, such as by using Equation 3. At 604, if the target time has not been reached (e.g., less than 24 hours), process flow returns to 600 to continue activity monitoring. At 608, an AUC is derived from the accumulated activity data over the target time period. At 610, a daily average MET is determined from the AUC information of 608.

Variations on this technique are also possible. For example, at 602, the increment value can be specified by the user or caregiver in increments of approximately one second, to days, weeks or months. Another approach would be to compare the exertion level to a threshold value, and to monitor the number of times the threshold value is reached, or the length of time spent at an exertion level that is above the value. However, the AUC method provides considerably more detailed information about the exertion and its associated time frame. For example, the AUC method allows one to identify not only how long a particular activity level occurred, but at what time it occurred in relation to other activity levels, and to detect a period of sustained physical activity exceeding a specified exertion level during a specified duration. In certain examples, the general activity detector 110 can detect physical activity by the subject but either the exertion level is very low (e.g., below 20 mGs) or the activity lasts for a very short time (e.g., 2 minutes or less). During such times, in certain examples, the exertion measured by the general activity detector 110 or step counter 112 can be identified as occurring during a rest state.

Figure 7:
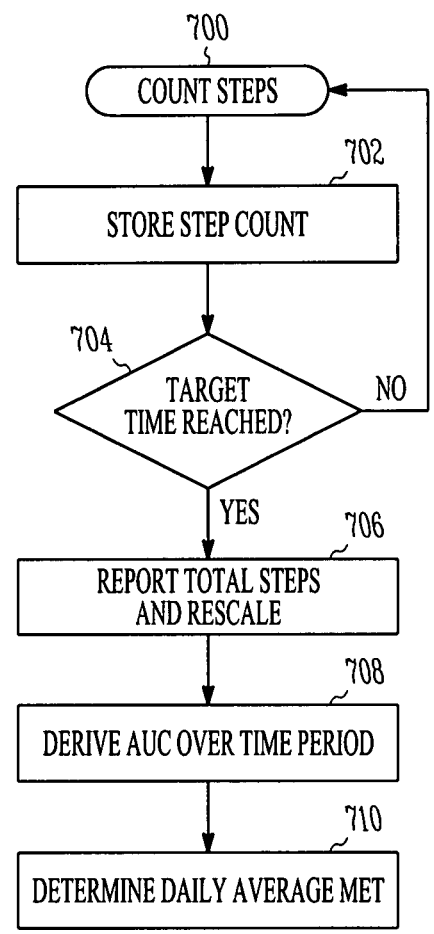
FIG. 7 is a diagram illustrating generally an example of portions of a technique for monitoring average daily metabolic expenditure using a step counter.

FIG. 7 is a diagram, similar to FIG. 5, illustrating generally an example of how a daily average metabolic activity value can be derived from monitoring step counts of a subject. At 700, step counts are acquired from a sensor (e.g., pedometer) which are indicative of exertion level of the subject, such as at rest, walking or running. At 702, data obtained from the step counter (e.g., total number of steps) is stored and can be associated with a time of occurrence. In certain examples, the clock 114 provides input to the processor for generating a time stamp. At 704, if a target time period for counting steps is reached (e.g., 24 hours have passed), then at 706, the stored total steps is reported and the number is converted to a METs equivalent, such as by using Equation 3. At 704, if the target time has not been reached (e.g., less than 24 hours), process flow returns to 700 to continue activity monitoring. At 708, an AUC is derived from the accumulated activity data over the target time period. At 710, a daily average MET is determined from the AUC information of 708.

Figure 8:
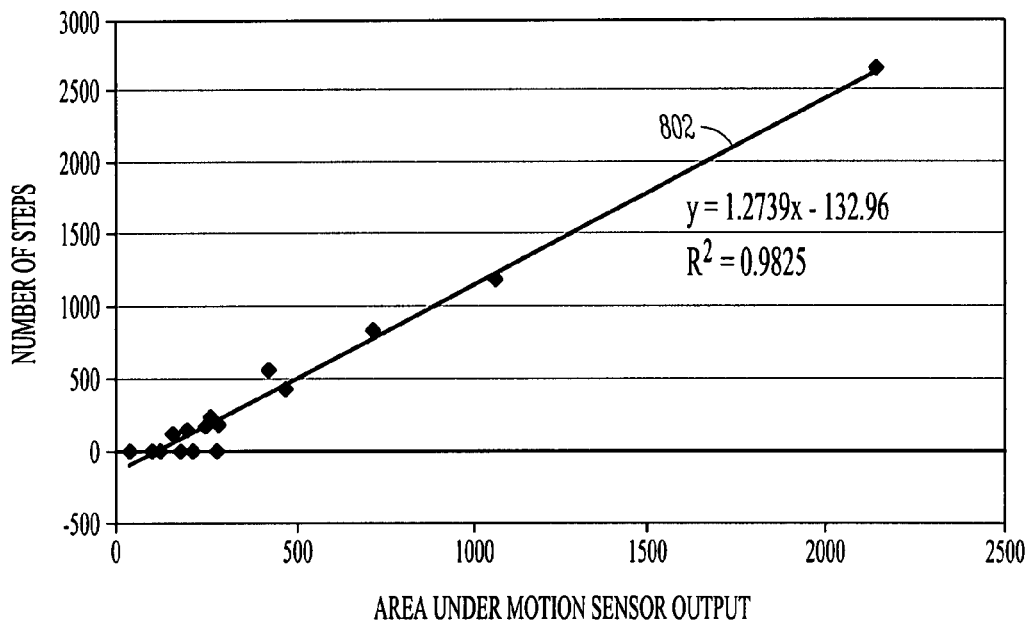
FIG. 8 is a simulation data graph illustrating generally an example of step counts correlated against integration of motion sensor output using area under the curve.

FIG. 8 is a simulation data graph illustrating generally step counts correlated against integration of motion sensor output using area under the curve. The graphical representation allows the user or caregiver to determine if step counts can correlate to measured exertion when two different activity sensors are used, such as an accelerometer in conjunction with a pedometer. The correlation plot 802 indicates a best fit among the data showing high correlation (e.g., $R^2$=0.9825). Therefore, in this example, increased total step counts correlate well with increased AUC of exertion levels.

Figure 9:
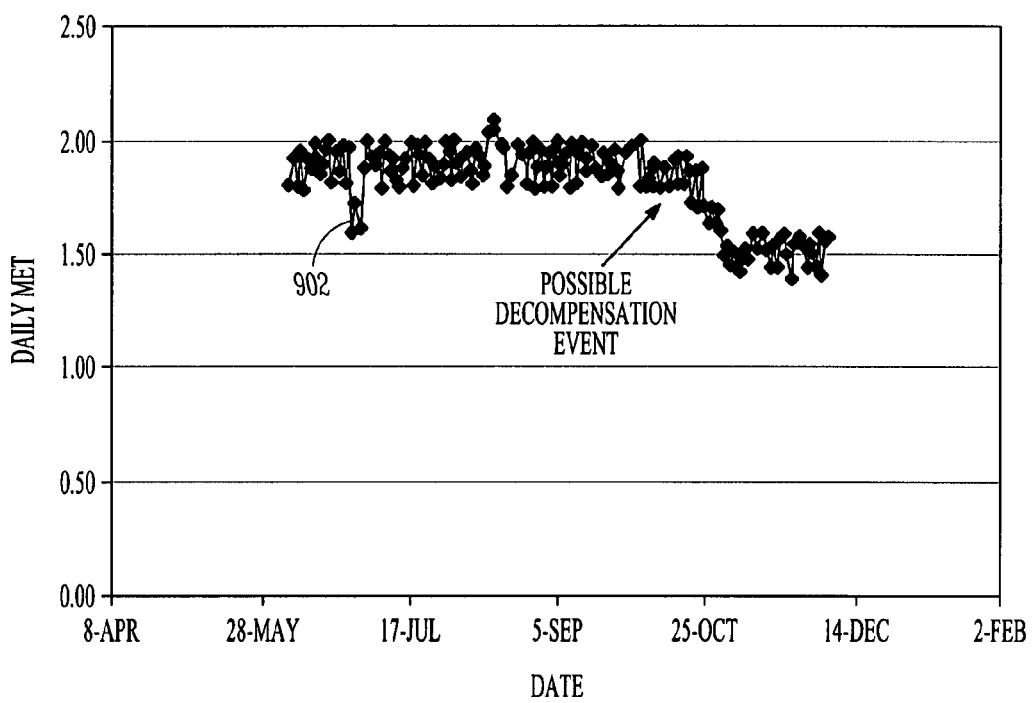
FIG. 9 is a simulation data graph showing an example of average daily METs logged over a period of months.

FIG. 9 is a simulation data graph showing average daily METs logged over a period of months. The plot 902 indicates consistency over a period of months in which activity is within a range of about 1.8 to 2.0 METs with the exception of late June or early July in which the METs drops to about 1.6. However, an interesting point in the plot is the adjustment in late October in which the range drops to 1.4 to 1.6 METs. This information could provide an indication that a CHF decompensation event may have occurred, and may alert the caregiver that the subject's condition could be deteriorating. Alternatively or additionally, in the example of FIG. 1, the alert response module 116 can provide closed-loop feedback to a therapy controller 118, which can initiate or adjust one or more congestive heart failure (CHF) or other therapies to be automatically delivered to the patient, such as cardiac resynchronization therapy (CRT), drug delivery, or any other suitable responsive therapy. Examples of CRT include, without limitation, adjusting AV delay, adjusting interventricular pacing delay, adjusting intraventricular pacing delay, adjusting intraventricular electrode selection, adjusting cardiac contractility modulation (CCM) therapy, or the like. For example, a rate-responsive pacer may already include a general accelerometer-based activity detector to determine a patient activity level, so that the pacing rate can be adjusted according to the patient activity level to adjust cardiac output according to a perceived metabolic need for such cardiac output. In certain examples, physical activity exceeding an exertion level or being sustained for a duration specified by a user can be used to determine physical activity has occurred. For example, an exertion exceeding 20 mGs for a duration exceeding three minutes may indicate physical activity. In other examples, a range of 20-30 mGs may indicate a walking subject.

Although the above description has emphasized an example in which processing is generally carried out within an implantable device, information derived from the respiration signal obtained from the implantable device can be communicated to external local interface 104 or external remote server 106 to perform such processing at such other locations. Moreover, such processing can include information from one or more devices that are not implanted. For example, a body weight measurement, as measured by an external weight scale, could be combined with a general activity detector obtained from an implantable cardiac function management device, e.g., during processing at external remote server 106, to generate a CHF wellness indicator or to trigger an alert or responsive therapy.

In certain examples, information from the processor 113 (e.g., indications of sudden onset of increased or decreased activity levels) can be provided to the communication module 103, and communicated to the external local interface 104 or the external remote server 106, such as for storage or for display on a monitor, for example, as separate trends of metabolic daily averages derived from step counts or exertion data, or as histograms of normalized daily average METs, or in any other useful form.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B," includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
   an activity detector, configured to:
      detect a physical movement by a subject; and
      measure exertion data, indicating an exertion level of the subject, measured from the detected physical movement by the subject;
   a processor circuit, coupled to the activity detector, the processor configured to analyze the exertion data from the activity detector, the processor configured to determine a metabolic stress indicator derived from an integration or area under the curve calculation of the measured exertion data occurring during the exertion within a time period; and
   an alert response module operatively coupled to the processor circuit, the alert response module configured to generate an alert in response to the metabolic stress indicator meeting a specified criterion.

2. The system of claim 1, wherein the processor is configured to provide a normalized average metabolic equivalent indication to a user or automated process.

3. The system of claim 2, comprising a trending module, operatively coupled to the activity detector and processor circuit, the trending module configured to trend normalized average metabolic equivalent indication occurring two or more times within a specified duration.

4. The system of claim 1, wherein the activity detector is configured to detect a period of sustained physical activity exceeding a specified exertion level and a specified duration.

5. The system of claim 4, wherein the specified exertion level comprises at least 20 mGs.

6. The system of claim 4, wherein the specified duration comprises at least three minutes.

7. The system of claim 1, wherein the activity detector is configured to determine a total number of steps per day.

8. The system of claim 7, wherein the processor is configured to determine the metabolic stress level by comparing the exertion data over a specified range, wherein the range comprises an upper bound corresponding to a maximum metabolic expenditure level of the subject and a lower bound corresponding to a minimum metabolic expenditure level of the subject.

9. The system of claim 1, wherein the activity detector is configured to determine a daily average MET using measured exertion data wherein the exertion data is obtained in increments of less than one minute.

10. The system of claim 1, comprising a therapy controller configured to initiate or adjust a therapy in response to the metabolic stress indicator meeting a specified criterion.

11. The system of claim 10, wherein the specified time duration comprises at least two days.

12. The system of claim 1, comprising an accelerometer, configured to:
   detect the physical movement by the subject; and
   provide an accelerometer output signal indicating the physical movement by the subject.

13. The system of claim 1, wherein the processor is configured to determine the metabolic stress level by comparing the exertion data to a threshold value, wherein the metabolic stress level corresponds to a number of times the threshold value is reached.

14. The system of claim 1, wherein the processor is configured to determine the metabolic stress level by comparing the exertion data to a threshold value, wherein the metabolic stress level corresponds to a duration for which the exertion data meets or exceeds the threshold value.

15. A method comprising:
- detecting a physical movement by a subject within a time period using an activity detector;
- measuring exertion data using the activity detector, the exertion data indicating an exertion level of the subject using the detected physical movement by the subject within the period;
- determining a metabolic stress indicator using a processor circuit, the metabolic stress indicator derived from an indication of an integration or area under the curve of the exertion data over the period; and
- generating an alert, using an alert response module, in response to the metabolic stress indicator meeting a specified criterion.

16. The method of claim 15, comprising providing a normalized average metabolic equivalent indication to a user or process.

17. The method of claim 16, comprising trending the normalized average metabolic equivalent indication.

18. The method of claim 15, wherein detecting physical activity comprises detecting a period of sustained physical activity exceeding a specified exertion level and a specified duration.

19. The method of claim 18, wherein the specified exertion level comprises at least 20 mGs.

20. The method of claim 18, wherein the specified duration comprises at least three minutes.

21. The method of claim 15, comprising determining a step rate derived from an averaged acceleration measurement of the subject movement over the period.

22. The method of claim 15, comprising deriving a metabolic equivalent (MET) from an acceleration within the period.

23. The method of claim 15, wherein determining a metabolic stress indicator comprises deriving a step total energy derived from the detected physical activity within the period.

24. The method of claim 15, comprising measuring at least one physiological parameter during the detected physical activity of the subject, wherein the measured physiological parameter varies with physical activity of the subject, and reporting the physiological parameter measurement to a user or automated process.

25. The method of claim 16, wherein providing a normalized average metabolic equivalent indication comprises deriving a number representative of average metabolic equivalent (MET) over the period.

26. The method of claim 15, comprising initiating or adjusting a therapy in response to the metabolic stress indicator meeting a specified criterion.

27. The method of claim 26, wherein the specified time duration comprises at least two days.

28. The method of claim 15, wherein determining a metabolic stress indicator comprises deriving a value representative of a population.

29. The method of claim 15, wherein determining a metabolic stress indicator comprises deriving a value representative of the subject.

* * * * *